United States Patent
Moretti

(10) Patent No.: US 6,350,782 B1
(45) Date of Patent: Feb. 26, 2002

(54) USE OF BASIC AMINO ACIDS DERIVATIVES FOR LOWERING CERAMIDE LEVELS

(75) Inventor: Sonia Moretti, Rome (IT)

(73) Assignees: Sigma-Tau Industrie Farmaceutiche Riunite S.p.A.; Mendes S.r.l., both of Rome (IT)

( * ) Notice: Subject to any disclaimer, the term of this patent is extended or adjusted under 35 U.S.C. 154(b) by 0 days.

(21) Appl. No.: 09/558,860

(22) Filed: Apr. 27, 2000

Related U.S. Application Data

(63) Continuation of application No. 09/000,203, filed as application No. PCT/IT96/00147 on Jul. 19, 1996, now Pat. No. 6,114,385.

(30) Foreign Application Priority Data

Aug. 3, 1995 (IT) .......................................... RM95A0545

(51) Int. Cl.[7] ................................................ A61K 31/22
(52) U.S. Cl. ........................ 514/551; 514/561; 514/171
(58) Field of Search ................................... 514/551, 561, 514/171

(56) References Cited

U.S. PATENT DOCUMENTS

| | | |
|---|---|---|
| 6,037,372 A | 3/2000 | Moretti |
| 6,040,346 A | 3/2000 | Moretti |
| 6,114,385 A | 9/2000 | Moretti |

*Primary Examiner*—Rebecca Cook
(74) *Attorney, Agent, or Firm*—Oblon, Spivak, McClelland, Maier & Neustadt, P.C.

(57) ABSTRACT

The present invention provides methods for treating a cellular disorder in a mammal which is induced by elevated levels of ceramide by administering a basic amino acid, acylated basic amino acid, or a pharmaceutically acceptable salt thereof to effectuate lowering the ceramide levels in the mammal.

8 Claims, No Drawings

USE OF BASIC AMINO ACIDS DERIVATIVES FOR LOWERING CERAMIDE LEVELS

This application is a Continuation of application Ser. No. 09/000,203. Filed on Feb. 3, 1998, now U.S. Pat. No. 6,114,385 which was originally filed as International Application Number PCT/IT96/00147 on Jul. 19, 1996.

The present invention relates to a novel therapeutic use of basic aminoacids, acylated basic aminoacids and their pharmacologically acceptable salts for the prophylaxis of diseases or the therapeutic treatment of cellular disorders accompanied by high levels of ceramide. In particular, the present invention relates to the use of L-carnitine, acyl L-carnitine derivatives and pharmacologically acceptable salts thereof for the prophylaxis of diseases or the therapeutic treatment of cellular disorders accompanied by high levels of ceramide.

Ceramide is the basic molecule for the sphingolipids structure and metabolism thereof. All sphingolipids contain ceramide as main hydrophilic component and originate from ceramide through biosynthesis pathways which mainly modify the 1-hydroxy position thereof. In turn, sphingolipids play an important role in the transduction of the signal across the cellular membrane.

Ceramide plays an important role in the transduction of the signal across the cellular membrane. Molecules able to act upon the intracellular receptors (i.e. calcitriol) or the transmembrane receptors [i.e., gamma interferon (IFN-γ), interleukin-1 (IL-1) and the nerve growth factor (NGF)] hydrolize sphingomyelin to ceramide. Ceramide activates phosphatases and protein kinases and, from a biological point of view, induces cellular apoptosis, growth and cell differentiation, modulates the expression of cyclooxygenases and phospholipases and the activation of kB nuclear factors (NFkB) [Kuno, K. et al., J. Leukoc. Biol., 56(5): 542–7; Cifone, M. G. et al., J. Exp. Med., 180(4): 1547–52; Kolesnick R., Mol. Chem. Neuropathol., 21(2–3): 287–97; Jarvis, W. D. et al., Proc. Natl. Acad. Sci. U.S.A, 91(1): 73–7; Obeid, L. M. et al., Science, 259(5102): 1769–71].

It has now been found that variations in the concentration or in the metabolism of ceramide contribute to the pathogenesis of numerous illnesses or contribute to induce metabolic cellular disorders. Unfortunately, to date, there exist no methods to reduce ceramide levels in vivo.

Accordingly, one object of this invention is to provide a novel use of basic aminoacids, acylated basic aminoacids and their pharmacologically acceptable salt for reducing ceramide levels in vivo.

A second object of the present invention is to provide a novel use of basic aminoacids, acylated basic aminoacids and their pharmacologically acceptable salt for the prophylaxis of diseases or the therapeutic treatment of cellular disorders accompanied by high levels of ceramide.

It has in fact been found that administration of high doses of basic aminoacids, low molecular weight basic compounds or acyl derivatives thereof and pharmacologically acceptable salts thereof reduces ceramide levels and such compounds can thus be used for the treatment of diseases characterized by high levels of ceramide.

In particular, it has been found that basic aminoacids such as arginine, lysine, histidine, ornithine, and carnitine or acyl derivatives thereof and pharmacologically acceptable salts thereof can be used for the treatment of diseases characterized by high levels of ceramide.

In accordance with the invention, a novel use of basic aminoacids, basic aminoacid acyl derivatives and pharmacologically acceptable salts thereof is provided for lowering the levels of ceramide in vivo.

Suitable aminoacids include any aminoacid with a basic charge such as arginine, lysine, histidine, ornithine and carnitine. These compounds are commercially available. Preferably, L-aminoacids are used. More preferably, carnitine is used. These compounds can be used as free aminoacids or as pharmaceutically acceptable salts.

Acyl derivatives of basic aminoacids can also be used in the present invention. $C_{2-6}$ acyl aminoacids which are linear or branched can be used. These acids are well known to the pharmacologists and to the skilled of pharmaceutical technique. Particularly preferrred acyl groups are acetyl, propionyl, butyryl, valeryl and isovaleryl.

Suitable pharmaceutical salts can be formed between the above basic aminoacids and any conventional anion such as chloride, bromide, iodide or an acid aspartate such as aspartate, an acid citrate such as citrate, an acid tartrate such as tratrate, an acid phosphate such as phosphate, an acid fumarate, a glycophosphate such as gluco-phosphate, acid lactate, acid maleate, orotate; acid oxalate, particularly oxalic acid; a sulfate, particularly preferably sulfate, trichloroacetate, trifluoroacetate and methanesulfonate.

Examples of illnesses or disorders characterized by elevated levels of ceramide include inflammatory bowel diseases, diffuse intravascular coagulation, fever, protein catabolism and/or lipid depletion, hepato-splenomegaly associated with inflammatory or metabolic liver diseases, endo-myocarditis, endothelial cells and leucocytes activation, capillary thrombosis, meningo-encephalitis due to infectious agents, organ transplantation, rheumatoid arthritis and connective tissue diseases, and autoimmune diseases, hyperthyroidism, damages by radiations and/or chemotherapy agents and chronic fatigue syndrome.

Since the use of some drugs can also induce high levels of ceramide, the present invention also contemplates decreasing ceramide levels in patients treated with such a drug. For example, a basic aminoacid in accordance with the present invention can be coadministered with corticoseroids (such as dexamethasone), anti-inflammatory (such as indomethacin), antiviral (such as interferon), immunosuppressants (such as cyclosporin), chemotherapy agents (such as adriamicin), immunopotentiants (such as immunoglobulins and vaccines) and endocrinological agents (such as metimazole) to prevent increased levels of ceramide.

Normal levels of ceramides in healthy patients depend on the age, size and weight of the individual, but are in general within the range of from 5 to 50 picomoles/$10^6$ cells preferably, lymphocytes of peripheral blood). Levels higher than 50 picomoles/$10^6$ cells are regarded as high levels. The use of basic aminoacids, acylated basic aminoacids and pharmacologically acceptable salts thereof of the present invention reduce such high levels by at least 25%.

In general, the basic aminoacids are administered in accordance with the present invention in concentrations which reduce ceramide levels by at least 25%. Suitably, this result is achieved by administering 50 mg to approximately 15 g/day of basic aminoacids by oral or parenteral route. Preferably, high levels of these basic aminoacids should be administered, i.e., >1 g per day, >2 g per day; particularly preferably, 4–10 g per day.

Monitoring ceramide levels can be conducted either by directly monitoring ceramide levels in a cell (such as a lymphocyte) or by indirectly monitoring the concentrations of a ceramide metabolite in a cell. Preferably, the patient's ceramide levels are monitored both prior to and following administration of the basic aminoacid in order to assess the amount of reduction. Monitoring can begin any time following administration but suitably is commenced following 3 hours to ensure accurate results. Monitoring can be continued indefinitely.

Ceramide levels can be directly measured by isolating peripheral blood lymphocytes from the patient. Thereafter the cells are centrifuged to eliminate the supernatant, and the lipids are removed from the cell pellet. The organic phase containing the ceramide can be assayed using the "DAG kinase assay" for phosphorylating the ceramide which is then evidenced by autoradiography [Cifone, M. G. et al., J. Exp. Med., 180(4): 1547–52].

Having generally described this invention, a further understanding can be obtained by reference to certain specific examples which are provided herein for purposes or illustration only and are not intended to be limiting unless otherwise specified.

EXAMPLE 1

Peripheral blood lymphocytes were isolated according to the classical methodologies. The cells were incubated with L-carnitine (200 mcg/ml) or with isovaleryl L-carnitine for 30 min at 37° C., and afterwards with an anti-Fas monoclonal antibody for another 30 min. The cells were then centrifuged, eliminating the supernatant, and the cell pellet was delipidized. The organic phase (containing the ceramide) was assayed in the "DAG kinase assay" for phosphorylating ceramide which subsequently was evidenced by autoradiography.

The results are indicated below in Table 1.

TABLE 1

| | Ceramide (picomoles per $10^6$ cells) |
|---|---|
| Control | 20 |
| Control + anti-Fas antibody | 81.6 |
| Control + anti-Fas antibody + L-carnitine (100 mcg/ml) | 7.3 |
| Control + anti-Fas antibody + isovaleryl L-carnitine (50 mcg/ml) | 8.6 |
| Control + anti-Fas antibody + isovaleryl L-carnitine (100 mcg/ml) | 7.3 |

It is known that the cells suitably stimulated (i.e. with Fas-L, inter-leukin-1, etc.) generate ceramide. An anti-Fas antibody was employed to increase the production of ceramide from a basal value (20 picomoles per $10^6$ cells) to 81.6 picomoles per $10^6$ cells.

L-carnitine and isovaleryl L-carnitine are thus shown to inhibit the synthesis of ceramide in vitro.

EXAMPLE 2

Two patients affected by symptomatic neuro-myopathy (chronic fatigue syndrome) were treated with 3 g per clay of L-carnitine by oral route through two months.

Ceramide was measured in the muscles before and after the administration.

The results are indicated below in Table 2.

TABLE 2

| | Ceramide pre-treatment (picomoles per mg of proteins) | Ceramide post-treatment (picomoles per mg of proteins) |
|---|---|---|
| Patient 1 | 76 | 28 |
| Patient 2 | 142 | 46 |

Four patients affected by hyperthyroidism who had been treated with metimazole (15 mg by oral route, daily) for more than eight months, were treated for 4 weeks with 8 g per day L-carnitine by oral route.

The lymphocyte-associated ceramide was determinded before and after the treatment.

The results are shown in the Table 3 which follows.

TABLE 3

| | Ceramide pre-treatment (picomoles/$10^6$ cells) | Ceramide post-treatment (picomoles/$10^6$ cells) |
|---|---|---|
| Patient 1 | 73 | 26 |
| Patient 2 | 45 | 27 |
| Patient 3 | 111 | 36 |
| Patient 4 | 69 | 18 |

EXAMPLE 4

Three patients with hepato-splenomegaly due to viral hepatitis of C type were treated with 4 g of L-carnitine bolus by intravenous route.

The lymphocyte-associated ceramide was determined before and after 3 and 48 hours following the infusion.

The results are shown in the Table 4 which follows.

TABLE 4

| | Patient 1 Ceramide (picomoles/$10^6$ cells) | Patient 2 Ceramide (picomoles/$10^6$ cells) | Patient 3 Ceramide (picomoles/$10^6$ cells) |
|---|---|---|---|
| Pre-treatment | 65 | 77 | 79 |
| After 3 hrs | 12 | 32 | 24 |
| After 48 hrs | 31 | 21 | 23 |

It is apparent that the administration of a bolus of L-carnitine inhibited the increase of ceramide levels already after 3 hours from the infusion. The effect remains at least for two days.

EXAMPLE 5

Four patients affected by protein catabolism and lipidic depletion as a consequence of tubercular infection were treated for two weeks with 8 g per day L-carnitine by parenteral route.

The peripheral blood lymphocyte-associated ceramide was determined before and after the treatment.

The results are shown in the Table 5 which follows.

TABLE 5

|  | Ceramide pre-treatment (picomoles/$10^6$ cells) | Ceramide post-treatment (picomoles/$10^6$ cells) |
|---|---|---|
| Patient 1 | 127 | 59 |
| Patient 2 | 265 | 77 |
| Patient 3 | 301 | 152 |
| Patient 4 | 78 | 54 |

Having now fully described the invention, it will be apparent to one of ordinary skill in the art that many changes and modifications can be made thereto without departing from the spirit or scope of the invention as claimed herein.

What is claimed is:

1. A method for treating a cellular disorder in a mammal which is induced by elevated levels of ceramide, comprising administering at least one basic amino acid, or an acylated basic amino acid, or a pharmaceutically acceptable salt thereof, to a mammal in an amount effective to lower ceramide levels, wherein said basic amino acid is selected from the group consisting of arginine, lysine, histidine and ornithine.

2. The method of claim 1, wherein said cellular disorder is selected from the group consisting of: inflammatory bowel disease, diffuse intravascular coagulation, capillary thrombosis, meningo-encephalitis due to infectious agents, connective tissue diseases, and damage by radiation.

3. The method of claim 1, further comprising the co-administration of a corticosteroid, an anti-inflammatory, an anti-viral agent, an immunosuppressant agent, a cryostatic agent, an immunopotentiant agent, or an endocrinological agent.

4. The method of claim 1, wherein the compound has a acyl group selected from the group consisting of: acetyl, propionyl, butyryl, valeryl and isovaleryl.

5. The method of claim 1, wherein the compound is a pharmacologically acceptable salt selected from the group consisting of chloride, bromide, iodide, acid aspartate, acid citrate, acid tartrate, acid phosphate, acid fumarate, glycophosphate, acid lactate, acid maleat, orotate, acid oxalate and sulfate.

6. The method of claim 1, wherein the compound is a pharmacologically acceptable salt selected from the group consisting of sulfate, trichloroacetate, trifluoroacetate and methanesulfonate.

7. The method of claim 1, wherein said effective amount is a daily dose administered orally or parentally, from 50 mg to 15 g.

8. The method of claim 1, wherein said effective amount is a daily dose administered orally or parentally, from 4 to 10 g.

\* \* \* \* \*